(12) United States Patent
Möhlmann et al.

(10) Patent No.: US 11,924,731 B2
(45) Date of Patent: Mar. 5, 2024

(54) TELEMATICS CONTROL UNITS (TCUs) INCLUDING SENSORS FOR MONITORING VEHICLE INTERIORS

(71) Applicant: MOLEX CVS BOCHUM GMBH, Bochum (DE)

(72) Inventors: Ulrich Möhlmann, Eckental (DE); Nicola Henseler, Herne (DE)

(73) Assignee: MOLEX CVS BOCHUM GMBH, Bochum (DE)

( * ) Notice: Subject to any disclaimer, the term of this patent is extended or adjusted under 35 U.S.C. 154(b) by 164 days.

(21) Appl. No.: 17/409,844

(22) Filed: Aug. 24, 2021

(65) Prior Publication Data

US 2022/0070644 A1 Mar. 3, 2022

Related U.S. Application Data

(60) Provisional application No. 63/069,714, filed on Aug. 25, 2020.

(51) Int. Cl.
*H04W 4/90* (2018.01)
*A61B 5/00* (2006.01)
(Continued)

(52) U.S. Cl.
CPC ............. *H04W 4/90* (2018.02); *A61B 5/0205* (2013.01); *A61B 5/6893* (2013.01); *A61B 5/7282* (2013.01); *A61B 5/747* (2013.01); *B60K 35/00* (2013.01); *B60Q 9/00* (2013.01); *G01K 3/005* (2013.01); *A61B 5/024* (2013.01); *A61B 5/0816* (2013.01); *B60K 2370/178* (2019.05)

(58) Field of Classification Search
CPC ...... H04W 4/90; A61B 5/0205; A61B 5/6893; A61B 5/747; B60K 35/00; B60Q 9/00; G01K 3/005
See application file for complete search history.

(56) References Cited

U.S. PATENT DOCUMENTS

2015/0360617 A1 12/2015 Schulz et al.
2018/0315292 A1 11/2018 Pham
(Continued)

FOREIGN PATENT DOCUMENTS

CN 105843218 A 8/2016
CN 110654393 A 1/2020

OTHER PUBLICATIONS

Yang, Z, et al., "Monitoring Vital Signs Using Millimeter Wave", Mobile Ad Hoc Networking and Computing, ACM, Jul. 5, 2016, pp. 211-220.
(Continued)

*Primary Examiner* — Curtis B Odom

(57) ABSTRACT

Exemplary embodiments are disclosed of telematics or telecommunication control units (TCUs) modules that includes a TCU and one or more sensor arrays (e.g., mmWave sensors, temperature sensors, ambient light sensors, biometric sensors, cameras, proximity sensors, WiFi, touch sensors, microphones, etc.) for monitoring vehicle interiors (e.g., monitoring health conditions of occupants within a vehicle passenger interior, etc.). In exemplary embodiments, sensors may be combined or integrated with (e.g., embedded within, placed on TCU printed circuit board (PCB), directly connected with, mounted along a bottom or side of, etc.) the TCU.

20 Claims, 9 Drawing Sheets

(51) Int. Cl.
    *A61B 5/0205*     (2006.01)
    *B60K 35/00*     (2006.01)
    *B60Q 9/00*     (2006.01)
    *G01K 3/00*     (2006.01)
    *A61B 5/024*     (2006.01)
    *A61B 5/08*     (2006.01)

(56) References Cited

U.S. PATENT DOCUMENTS

| | | | |
|---|---|---|---|
| 2019/0025856 A1* | 1/2019 | Turato | B60W 10/06 |
| 2019/0143915 A1* | 5/2019 | Lei | B60R 16/0237 |
| | | | 701/29.2 |
| 2021/0229697 A1* | 7/2021 | Lee | G05D 1/0011 |
| 2023/0000441 A1* | 1/2023 | Narasimhan | A61B 5/0816 |

OTHER PUBLICATIONS

Extended European Search Report and Opinion received for EP Application No. 21193068.0, dated Feb. 1, 2022, 12 pages.

* cited by examiner

TELEMATICS CONTROL UNITS (TCUs) INCLUDING SENSORS FOR MONITORING VEHICLE INTERIORS

CROSS-REFERENCE TO RELATED APPLICATION

This application claims the benefit of and priority to U.S. Provisional Patent Application No. 63/069,714 filed Aug. 25, 2020, all of which is incorporated herein by reference in its entirety.

FIELD

The present disclosure generally relates to telematics control units (TCUs), more specifically for TCUs mounted in a vehicle.

BACKGROUND

This section provides background information related to the present disclosure which is not necessarily prior art.

Telematics control units (TCUs) are commonly placed inside the dash or engine compartment of a vehicle. The TCU can be connected to the infotainment hub as well as provide a network access device for the ECM and other vehicle subsystems. This location is convenient for access to systems that can benefit from access to a data connection to exterior systems but is inconvenient from a standpoint of actually connecting to the exterior. That is because the exterior of a vehicle substantially attenuates signals received and transmitted from the TCU. To overcome this issue, state of the art systems tend to use an exterior antenna (such as the rear mounted "shark fin" antenna common on many vehicles) to provide a better antenna system. To allow for improved performance, a cable extends between the TCU and the remote antenna. To allow for improved performance, a compensator system is often included to compensate for losses in the cable as the losses can vary depending on temperature. While this entire system works well, certain individuals would appreciate further improvements to reduce the cost of the system while providing for enhancement in capabilities.

DRAWINGS

The drawings described herein are for illustrative purposes only of selected embodiments and not all possible implementations, and are not intended to limit the scope of the present disclosure.

Corresponding reference numerals may indicate corresponding (although not necessarily identical) parts throughout the several views of the drawings.

DETAILED DESCRIPTION

Figure 1:
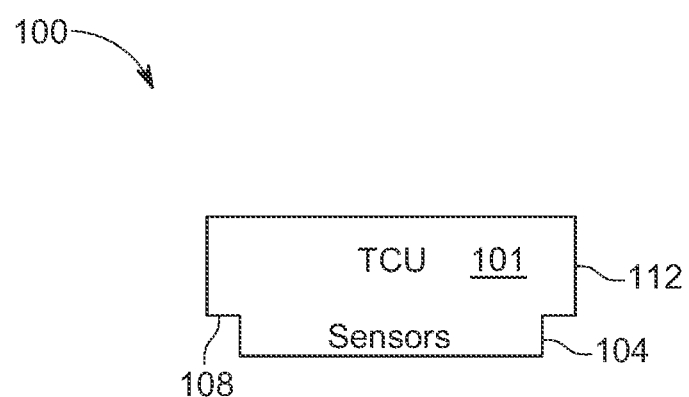
FIG. 1 illustrates a schematic view of sensors along a bottom of a telematics control unit (TCU) for monitoring a vehicle interior according to an exemplary embodiment.

Example embodiments will now be described more fully with reference to the accompanying drawings.

Conventionally, several sensors may be separately, individually installed at different places within a vehicle to monitor the vehicle's passengers or occupants. But as recognized herein, individually installing separate sensors at different places within a vehicle tends to have high manufacturing costs and high assembly effort.

Accordingly, disclosed herein are exemplary embodiments of telematics or telecommunication control units (TCUs) modules including sensors (e.g., mmWave sensors, temperature sensors, ambient light sensors, biometric sensors, cameras, proximity sensors, WiFi, touch sensors, microphones, etc.) for monitoring vehicle interiors (e.g., monitoring health conditions of occupants within a vehicle passenger interior, etc.). The sensors are integrated or combined with (e.g., embedded within, connected directly with, mounted along a bottom or side of, etc.) a TCU. The TCU module can be positioned in the ceiling of a vehicle (e.g., between a vehicle's roof and roof liner, etc.) so as to provide a line of sight between the sensors and passengers positioned in the vehicle.

For example, one or more sensors may be placed along a bottom and/or one or more sides of the TCU. Or, for example, one or more sensors may be electrically connected (e.g., via wires, cables, board-to-board (B2B) connectors, etc.) directly to the TCU. As another example, one or more sensors may be embedded within the TCU, e.g., placed along a printed circuit board of the TCU, etc. The one or more sensors may be disposed within the same interior space defined by a housing of the TCU as other various TCU components.

In exemplary embodiments, the sensors may be combined or integrated with the TCU such that TCU module may be installed within a vehicle collectively as a single combined and/or integrated unit. Advantageously, this may allow for the elimination of the need to separately, individually install a TCU and various sensors at different places within the vehicle.

In exemplary embodiments, the TCU module may be configured to enable the triggering of an eCall by monitoring heartbeat and/or breathing of vehicle occupants using mmWave sensor technology. In this example, the TCU module may include one or more mmWave sensors that transmit signals with a wavelength in the millimeter (mm) range and that may be configured to work through certain resins or other materials (e.g., plastics, clothing, vehicle roof liners, etc.). As another example, the TCU module may be configured to enable the automatic opening of a window and/or the automatic initiation of an alert (e.g., activating a car alarm, etc.) if an occupant (e.g., infant, dog, etc.) is detected in the vehicle and the temperature of the vehicle interior has exceeded a predetermined maximum temperature, etc. As a variety of sensors may be combined or integrated with (e.g., embedded within, directly connected to, mounted along a bottom/side of, etc.) a TCU, the TCU module may be configured to enable other additional and/or different uses in other exemplary embodiments.

In exemplary embodiments, combining and processing of the sensor data (e.g., sensor data fusion, etc.) may be performed by one or processors of the TCU. In such exemplary embodiments, the sensors are therefore not necessarily required to be smart/very intelligent sensors. The sensor data processing, algorithms, and/or applications that combine and process the information from the different sensors may operate or run within the TCU. And, the TCU may then drive, cause, or initiate the relevant actions, e.g., send the information/command "open window" to the window electronic control unit (ECU), etc.

With reference now to the figures, FIG. 1 illustrates an exemplary embodiment of a telematics or telecommunication control unit (TCU) module 100, which includes a TCU 101 and further includes a sensor array 104. As shown in FIG. 1, the sensor array 104 is positioned along a bottom 108 of the TCU 101. The sensor array 104 is configured for monitoring the vehicle interior when the TCU module 100 is mounted in or on the vehicle's roof. If the TCU module 100 includes a substrate that supports a processor of some type, for example, the sensor array 104 can be mounted directly on the substrate. Alternatively, the substrate could include a first connector that allows for a sensor connected to a second connector, the second connector mated with the first connector, to be electrically connected to the substrate.

The sensor array 104 may be coupled (e.g., adhesively attached, mechanically fastened, fixedly attached, etc.) to an exterior surface defined by a bottom 108 of a housing 112 of the TCU module 100. The housing may define, in whole or in part, an interior space in which are positioned various TCU components. In an embodiment, for example, the sensor array 104 may be disposed within the same interior space defined by the TCU housing 112 as the various TCU components. By mounting the sensor array 104 along the bottom 108 of the TCU module 100, the TCU 101 and the sensor array 104 may be installed within a vehicle collectively as a single combined and/or integrated unit, e.g., without having to separately and individually install the TCU 101 and the sensor array 104 within the vehicle, etc.

The sensor array 104 may comprise one or more sensors and if multiple sensors are included in the sensor array 104, then a variety of sensor types can be used for different sensors. In one exemplary embodiment, for example, the sensor array 104 includes a mmWave sensor and a temperature sensor. The mmWave sensor may be configured for monitoring health conditions (e.g., heart rate, breathing rate, etc.) of occupants within the vehicle's passenger interior. The temperature sensor may be configured for monitoring the temperature within the vehicle passenger interior. The sensor array 104 may include additional sensors, such as, without limitation, an ambient light sensor (to detect visibility), a glass breaking sensor (to detect breaking of a window), an airbag sensor that detects excitation of an airbag, and any other sensors (e.g., biometric sensor, camera, proximity sensor, WiFi, touch sensor, microphone, etc.) that is desired to be included in the sensor array 104. As the combination of sensors will vary depending on the desired functionality, it can be appreciated that any desired sensor array that includes the needed functionality can be used in combination with the TCUs discussed herein. Thus, the discussion of a sensor array is abbreviated in subsequent embodiments with the understanding that each structurally different embodiment of TCU can use the range of sensor arrays discussed herein.

The TCU housing 112 is configured to fit over the various TCU components such that the TCU components are within the interior space defined by the TCU housing 112. The TCU housing 112 is configured to protect the relatively fragile TCU components from damage due to environmental conditions, vibrations, shock during use, etc. By way of example, the TCU components may include one or more fans for air circulation, TCU electronics, printed circuit boards (PCBs), connectors, microprocessors, various electrical circuits, etc. The TCU housing 112 may be formed from a wide range of materials, such as polymers, urethanes, plastic materials (e.g., polycarbonate blends, Polycarbonate-Acrylonitrile-Butadiene-Styrene (PC/ABS) blend, etc.), glass-reinforced plastic materials, synthetic resin materials, thermoplastic materials (e.g., GE Plastics Geloy® XP4034 Resin, etc.), among other suitable materials.

Figure 2:
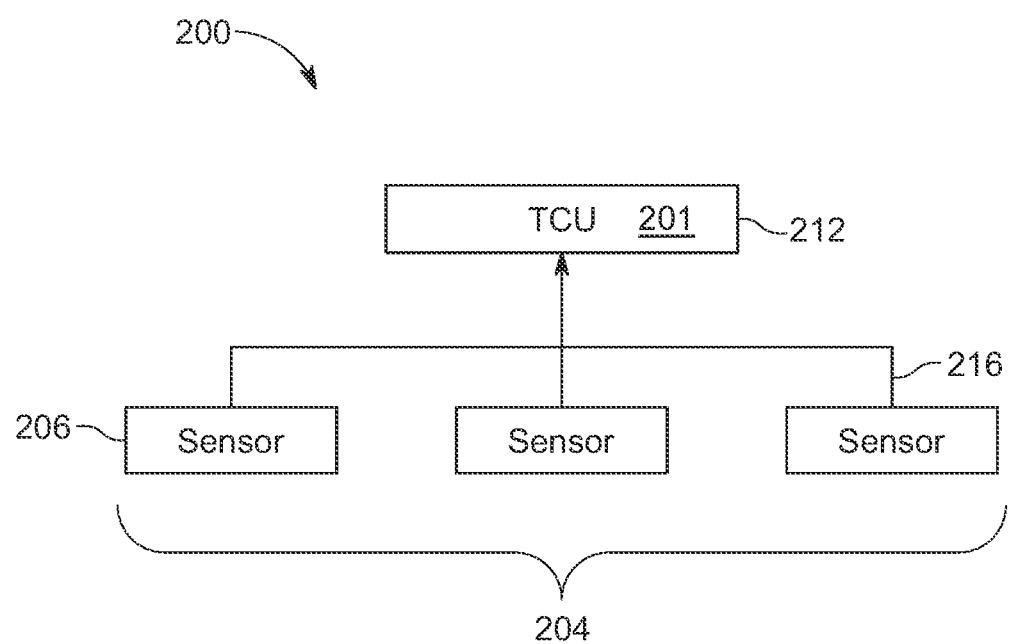
FIG. 2 illustrates a schematic view of sensors electrically connected to a TCU for monitoring a vehicle interior according to another exemplary embodiment.

FIG. 2 illustrates another exemplary embodiment of a TCU module 200 that includes a TCU 201 and a sensor array 204 (which as depicted includes three separate sensors 206). The sensor array 204 may be electrically connected to the TCU 201. For example, the sensor array 204 may be electrically connected to the TCU 201 by one or more wires or cables 216, etc. The sensor array 204 is configured for monitoring the vehicle's passenger interior when the TCU module 200 is mounted to the vehicle's roof.

As depicted in FIG. 2, the sensor array 204, which can be configured as discussed with respect to sensor array 104, is external to a housing 212 of the TCU 200. For example, the sensor array 204 may comprise one or more sensors and if multiple sensors are included in the sensor array 204, then a variety of sensor types can be used for different sensors. In one exemplary embodiment, for example, the sensor array 204 includes a mmWave sensor and a temperature sensor. The mmWave sensor may be configured for monitoring health conditions (e.g., heart rate, breathing rate, etc.) of occupants within the vehicle's passenger interior. The temperature sensor may be configured for monitoring the temperature within the vehicle passenger interior. The sensor array 204 may include additional sensors, such as, without limitation, an ambient light sensor (to detect visibility), a glass breaking sensor (to detect breaking of a window), an airbag sensor that detects excitation of an airbag, and any other sensors (e.g., biometric sensor, camera, proximity sensor, WiFi, touch sensor, microphone, etc.) that is desired to be included in the sensor array 204. As the combination of sensors will vary depending on the desired functionality, it can be appreciated that any desired sensor array that includes the needed functionality can be used in combination with the TCU discussed herein.

The housing 212 may define an interior space in which are positioned various TCU components. The housing 212 can be configured as discussed with respect to the housing 112.

As can be appreciated, the TCU 201 and the sensor array 204 may be configured to be installed within a vehicle collectively as a single combined and/or integrated unit, e.g., without having to separately, individually install the TCU 201 and each sensor of the sensor array 204 within the vehicle, etc. Alternatively, the housing 212 can include one or more connectors that allows the sensor array 204 to be readily connected to the housing 212.

Figure 3:
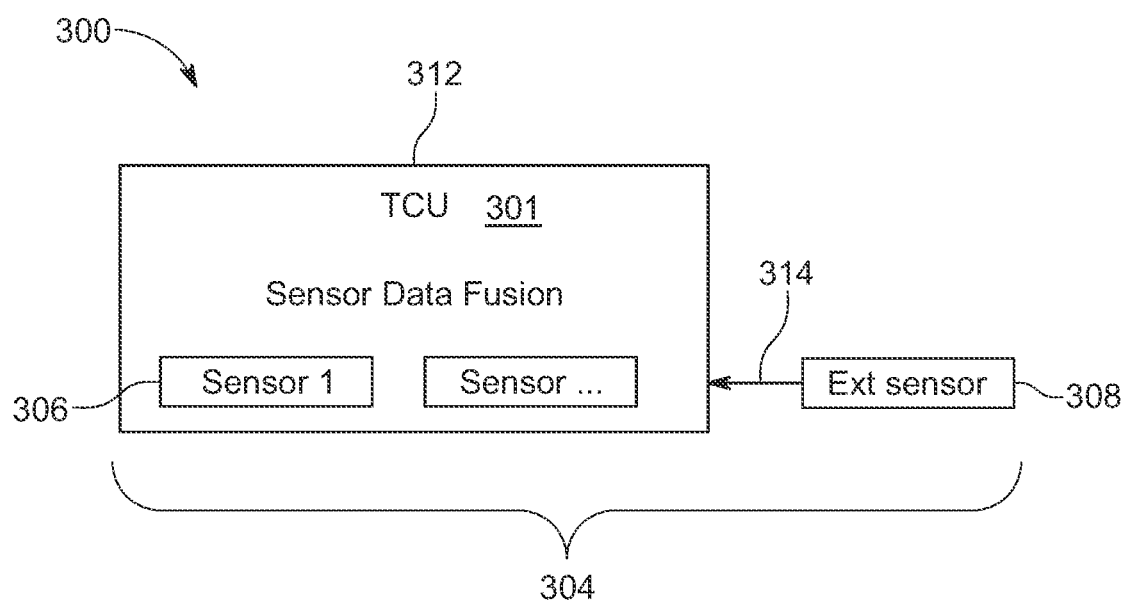
FIG. 3 illustrates a schematic view of sensors placed on a printed circuit board (PCB) of the TCU and an external sensor for monitoring a vehicle interior according to another exemplary embodiment.

FIG. 3 illustrates another exemplary embodiment of a TCU module 300 that includes a TCU 301 and further includes a sensor array 304 for monitoring a vehicle's passenger interior. As depicted in FIG. 3, the sensor array 304 includes two separate sensors 306 placed on a printed circuit board (PCB) of the TCU 301. The sensor array 304 also includes an external sensor 308, which may be electrically connected to the sensors 306 and/or TCU 301 by one or more wires or cables 314, etc. Advantageously, this exemplary embodiment shown in FIG. 3 may have a relatively low cost and/or relatively low manufacturing effort.

The sensor array 304 can be configured as discussed with respect to sensor array 104. For example, the sensor array 304 may comprise one or more sensors and if multiple sensors are included in the sensor array 304, then a variety of sensor types can be used for different sensors. In one exemplary embodiment, for example, the sensor array 304 includes a mmWave sensor and a temperature sensor. The mmWave sensor may be configured for monitoring health conditions (e.g., heart rate, breathing rate, etc.) of occupants within the vehicle's passenger interior. The temperature sensor may be configured for monitoring the temperature within the vehicle passenger interior. The sensor array 304 may include additional sensors, such as, without limitation, an ambient light sensor (to detect visibility), a glass breaking sensor (to detect breaking of a window), an airbag sensor that detects excitation of an airbag, and any other sensors (e.g., biometric sensor, camera, proximity sensor, WiFi, touch sensor, microphone, etc.) that is desired to be included in the sensor array 304. As the combination of sensors will vary depending on the desired functionality, it can be appreciated that any desired sensor array that includes the needed functionality can be used in combination with the TCU discussed herein.

The sensors 306 may be internal to a housing 312 of the TCU 300, while the external sensor 308 may be external to the housing our cover 312. The housing 312 may define an interior space in which are positioned various TCU components. The housing 312 can be configured as discussed with respect to the housing 112.

As can be appreciated, the TCU 301 and the sensor array 304 may be configured to be installed within a vehicle collectively as a single combined and/or integrated unit, e.g., without having to separately, individually install the TCU 301 and each sensor 306, 308 of the sensor array 304 within the vehicle, etc. Alternatively, the housing 312 can include one or more connectors that allows the sensor array 304 to be readily connected to the housing 312.

Figure 4:
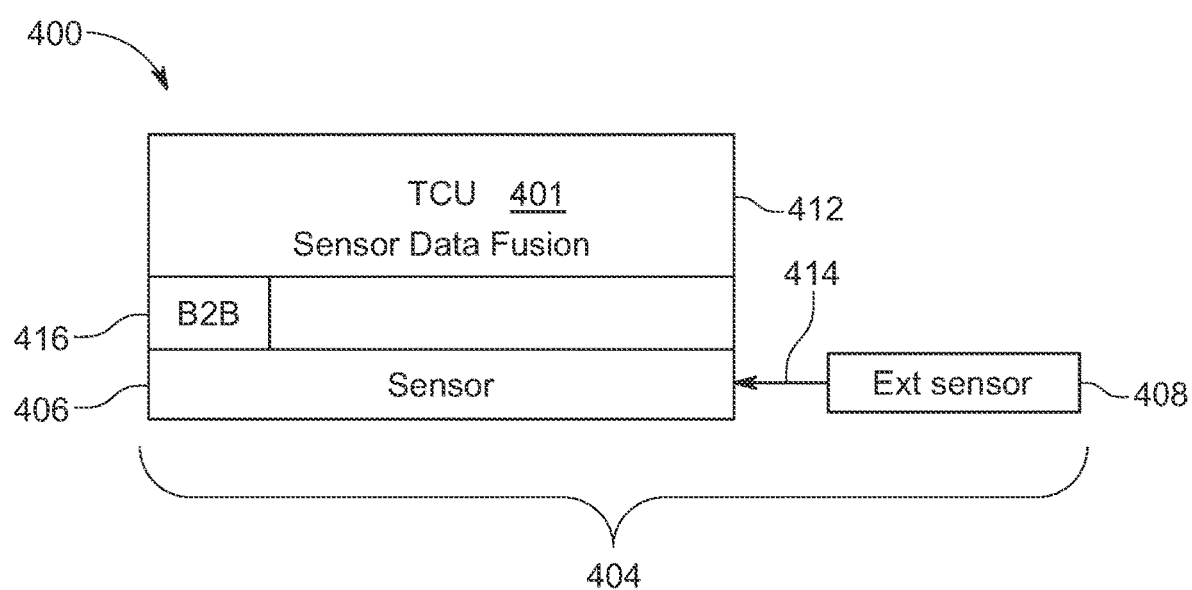
FIG. 4 illustrates a schematic view of sensor electrically connected via a board-to-board (B2B) connector to the TCU PCB and an external sensor for monitoring a vehicle interior according to another exemplary embodiment.

FIG. 4 illustrates another exemplary embodiment of a TCU module 400 that includes a TCU 401 and a sensor array 404 for monitoring a vehicle's passenger interior. As depicted in FIG. 4, the sensor array 404 includes sensors 406 and 408 electrically connected with the TCU 400. For example, the PCB of the sensor 406 may be electrically connected to the TCU 400 by a board-to-board (B2B) connector 416. The sensor 408 may be electrically connected to the sensor 406 and/or TCU 401 by one or more wires or cables 414. In this exemplary embodiment, the sensors 406, 408 are not placed on the TCU PCB, which may therefore save space on the TCU PCB for other components and/or allow a smaller TCU PCB to be used.

The sensor array 404 can be configured as discussed with respect to sensor array 104. For example, the sensor array 404 may comprise one or more sensors and if multiple sensors are included in the sensor array 404, then a variety of sensor types can be used for different sensors. In one exemplary embodiment, for example, the sensor array 404 includes a mmWave sensor and a temperature sensor. The mmWave sensor may be configured for monitoring health conditions (e.g., heart rate, breathing rate, etc.) of occupants within the vehicle's passenger interior. The temperature sensor may be configured for monitoring the temperature within the vehicle passenger interior. The sensor array 404 may include additional sensors, such as, without limitation, an ambient light sensor (to detect visibility), a glass breaking sensor (to detect breaking of a window), an airbag sensor that detects excitation of an airbag, and any other sensors (e.g., biometric sensor, camera, proximity sensor, WiFi, touch sensor, microphone, etc.) that is desired to be included in the sensor array 404. As the combination of sensors will vary depending on the desired functionality, it can be appreciated that any desired sensor array that includes the needed functionality can be used in combination with the TCU discussed herein.

The sensors 406 may be internal to a housing 412 of the TCU 401, while the external sensor 408 may be external to the housing our cover 412. The housing 412 may define an interior space in which are positioned various TCU components. The housing 412 can be configured as discussed with respect to the housing 112.

As can be appreciated, the TCU 401 and the sensor array 404 may be configured to be installed within a vehicle collectively as a single combined and/or integrated unit, e.g., without having to separately, individually install the TCU 401 and each sensor 406, 408 of the sensor array 404 within the vehicle, etc. Alternatively, the housing 412 can include one or more connectors that allows the sensor array 404 to be readily connected to the housing 412.

Figure 5:
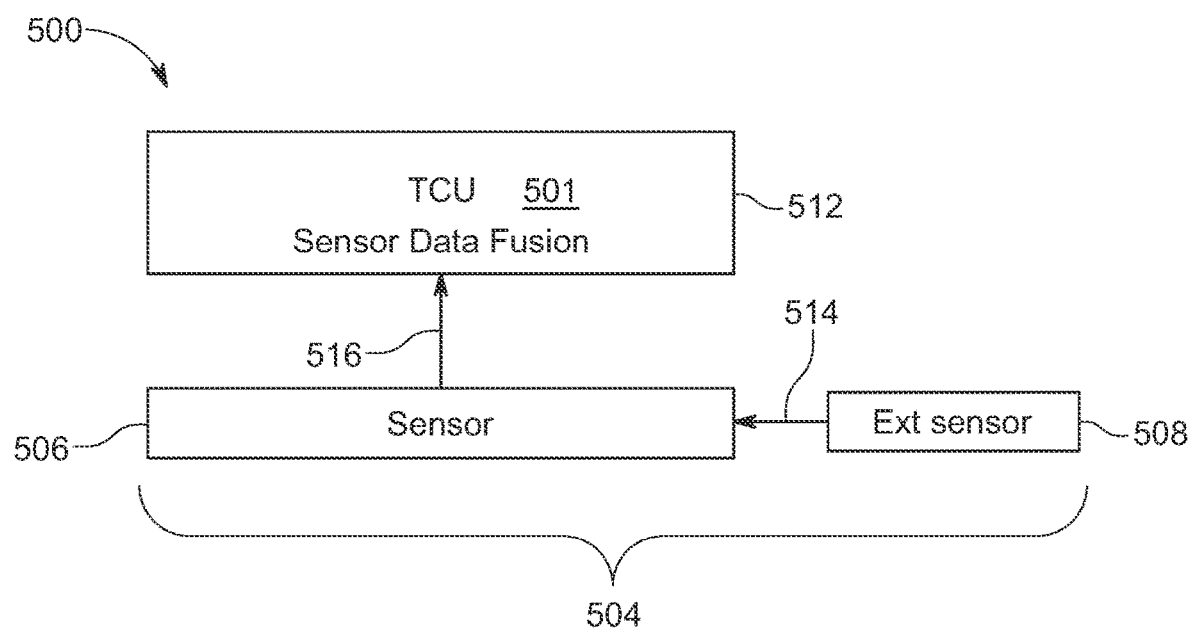
FIG. 5 illustrates a schematic view of sensor electrically connected with the TCU PCB and an external sensor for monitoring a vehicle interior according to another exemplary embodiment.

FIG. 5 illustrates another exemplary embodiment of a TCU module 500 with a TCU 501 and a sensor array 504 for monitoring a vehicle's passenger interior. As depicted in FIG. 5, the sensor array 504 includes sensor 506 and 508 electrically connected with the TCU 501. For example, the sensor 506 may be electrically connected to the TCU 501 by one or more wires or cables 516, etc. The sensor 508 may be electrically connected to the sensor 506 and/or TCU 501 by one or more wires or cables 514. In this exemplary embodiment, the sensor PCB may advantageously be placed in the middle of the vehicle, where the mmWave sensor is preferably installed.

The sensor array 504 can be configured as discussed with respect to sensor array 104. For example, the sensor array 504 may comprise one or more sensors and if multiple sensors are included in the sensor array 504, then a variety of sensor types can be used for different sensors. In one exemplary embodiment, for example, the sensor array 504 includes a mmWave sensor and a temperature sensor. The mmWave sensor may be configured for monitoring health conditions (e.g., heart rate, breathing rate, etc.) of occupants within the vehicle's passenger interior. The temperature sensor may be configured for monitoring the temperature within the vehicle passenger interior. The sensor array 504 may include additional sensors, such as, without limitation, an ambient light sensor (to detect visibility), a glass breaking sensor (to detect breaking of a window), an airbag sensor that detects excitation of an airbag, and any other sensors (e.g., biometric sensor, camera, proximity sensor, WiFi, touch sensor, microphone, etc.) that is desired to be included in the sensor array 504. As the combination of sensors will vary depending on the desired functionality, it can be appreciated that any desired sensor array that includes the needed functionality can be used in combination with the TCU discussed herein.

The sensors 506, 508 may be external to the housing our cover 512. The housing 512 may define an interior space in which are positioned various TCU components. The housing 512 can be configured as discussed with respect to the housing 112.

As can be appreciated, the TCU 501 and the sensor array 504 may be configured to be installed within a vehicle collectively as a single combined and/or integrated unit, e.g., without having to separately, individually install the TCU 501 and each sensor 506, 508 of the sensor array 504 within the vehicle, etc. Alternatively, the housing 512 can include one or more connectors that allows the sensor array 504 to be readily connected to the housing 512.

Figure 6:
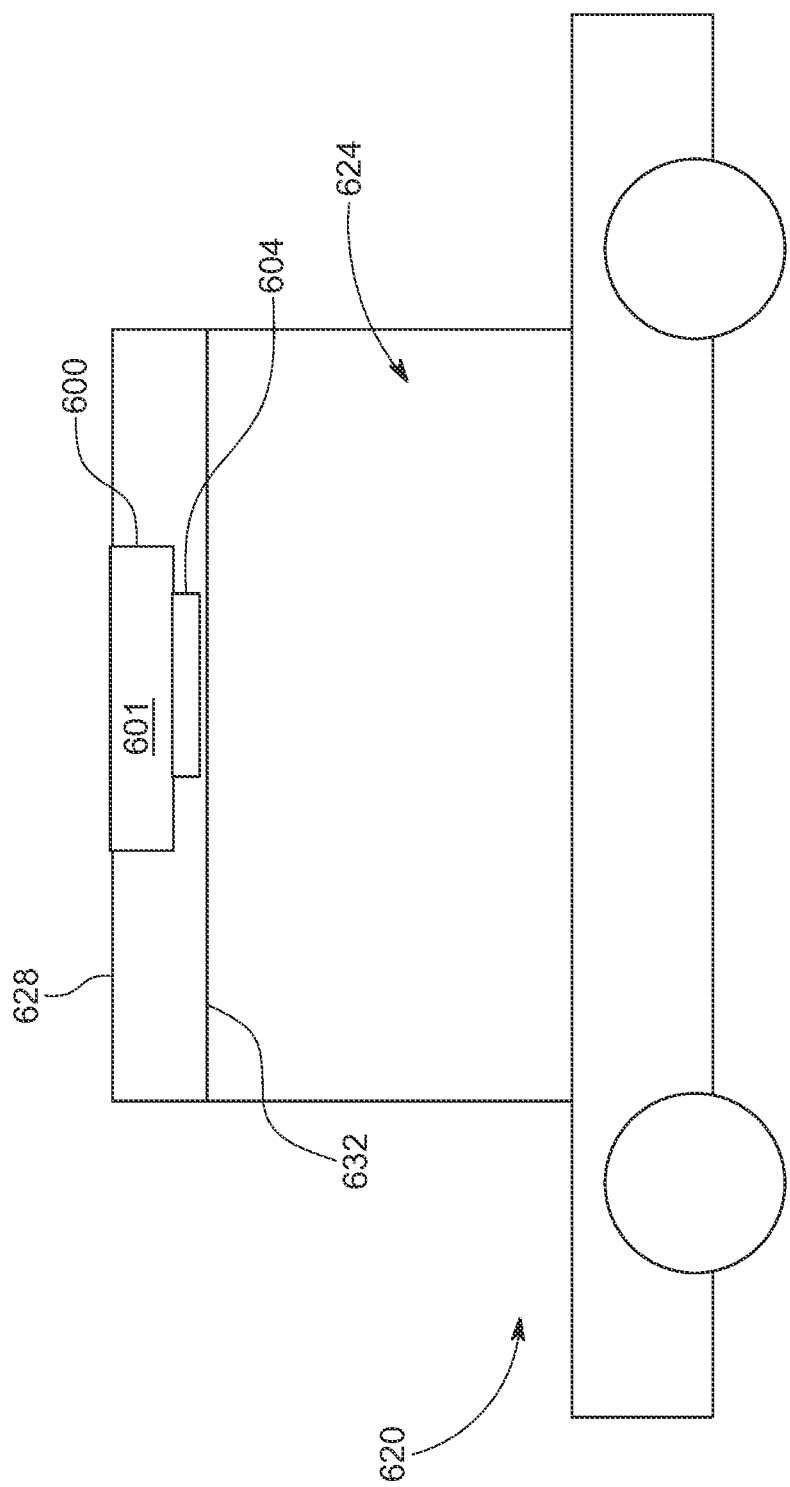
FIG. 6 illustrates a schematic view of a vehicle including a passenger interior, a roof, a roof liner, and a telematics control unit (TCU) including one or more sensors according to an exemplary embodiment.

FIG. 6 illustrates a vehicle 620 including a passenger interior 624, a roof 628, a roof liner 632, and a TCU module 600 with a TCU 601 connected to a sensor array 604. By way of example, the sensor array 604 may be combined or integrated with the TCU 601 as discussed herein and/or illustrated in the figures. For example, the sensor array 604 may be mounted along the bottom (e.g., FIG. 1, etc.) and/or one or more side(s) of the TCU 600. Or, the sensor array 604 may be electrically connected directly to the TCU 600, e.g., via wires or cables (e.g., FIG. 5, etc.), board-to-board (B2B) connectors (e.g., FIG. 4, etc.), etc.

The sensor array 604 can be configured as discussed with respect to sensor array 104 (FIG. 1). For example, the sensor array 604 may comprise one or more sensors and if multiple sensors are included in the sensor array 604, then a variety of sensor types can be used for different sensors. In one exemplary embodiment, for example, the sensor array 604 includes a mmWave sensor and a temperature sensor. The mmWave sensor may be configured for monitoring health conditions (e.g., heart rate, breathing rate, etc.) of occupants within the vehicle's passenger interior. The temperature sensor may be configured for monitoring the temperature within the vehicle passenger interior. The sensor array 604 may include additional sensors, such as, without limitation, an ambient light sensor (to detect visibility), a glass breaking sensor (to detect breaking of a window), an airbag sensor that detects excitation of an airbag, and any other sensors (e.g., biometric sensor, camera, proximity sensor, WiFi, touch sensor, microphone, etc.) that is desired to be included in the sensor array 604. As the combination of sensors will vary depending on the desired functionality, it can be appreciated that any desired sensor array that includes the needed functionality can be used in combination with the TCU discussed herein.

The TCU module 600 is preferably mounted to the vehicle roof 628, and the sensor array 604 is configured for monitoring the vehicle's passenger interior. As shown in FIG. 6, the TCU 601 and the sensor array 604 are positioned so that the roof liner 632 covers the sensor array 604. The TCU 601 and the sensor array 604 may be configured to be installed within the vehicle 620 collectively as a single combined and/or integrated unit, e.g., without having to separately, individually install the TCU 601 and the sensor array 604 within the vehicle 620, etc.

Figure 7:
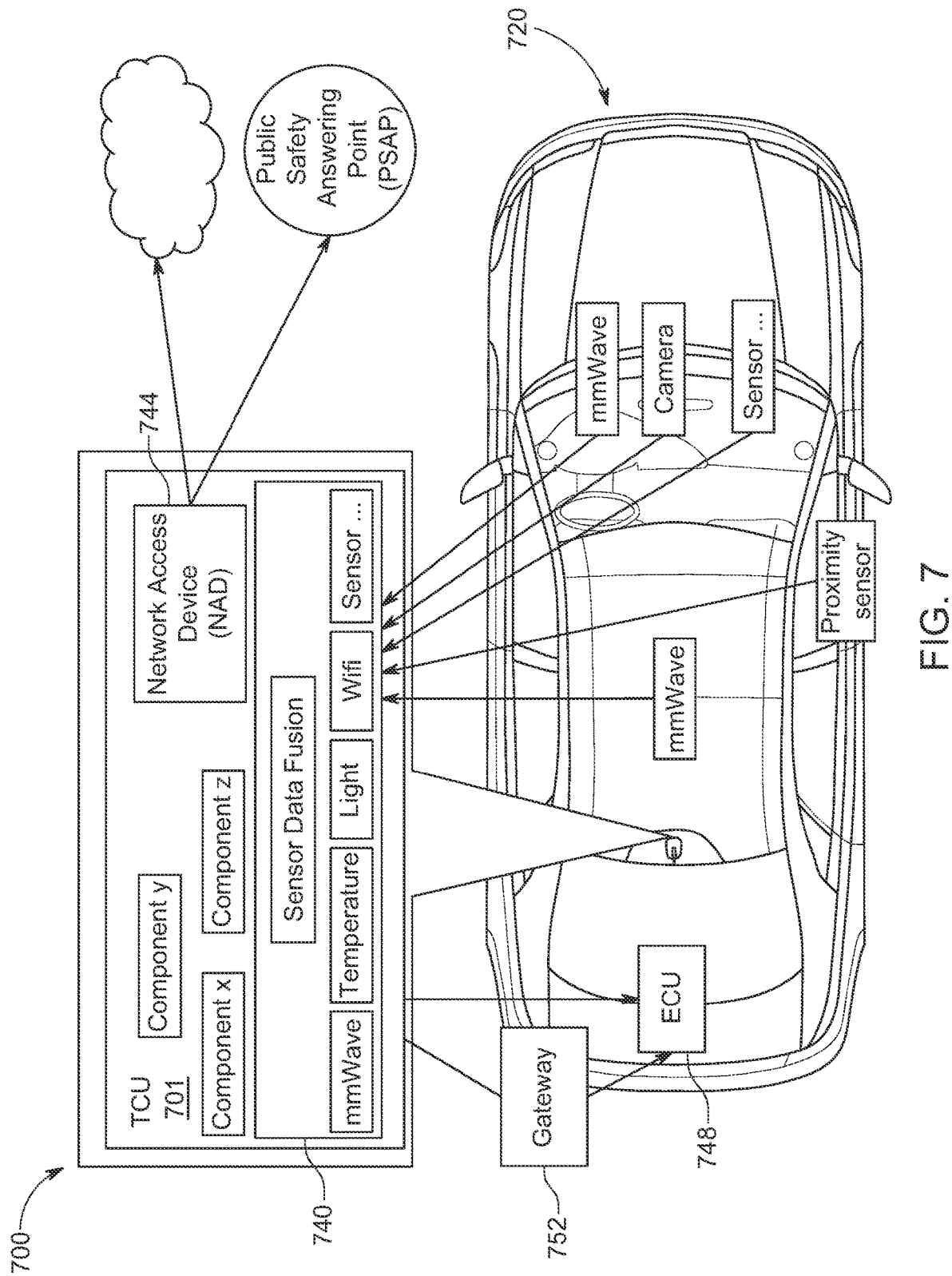
FIG. 7 illustrates a vehicle including a telematics control unit (TCU) and sensors for monitoring a vehicle interior according to another exemplary embodiment in which the TCU is configured for combining and processing the sensor data (e.g., sensor data fusion, etc.).

FIG. 7 illustrates a vehicle 720 including a TCU module 700 with a TCU 701 and a sensor array for monitoring the vehicle's interior according to another exemplary embodiment. As represented by Sensor Data Fusion 740 in FIG. 7, combining and processing of the sensor data obtained by the sensor array may be performed by one or more processors of the TCU 701. Accordingly, the various sensors (e.g., mmWave sensors, temperature sensor, light sensor, WiFi, camera, proximity sensor, touch sensor, microphone, etc.) are therefore not necessarily required to be smart or intelligent sensors, e.g., configured with data processing capabilities, etc. The sensor data processing, algorithms, and/or applications that combine and process the information from the different sensors of the sensor array may operate or run within the TCU 701. And, the TCU 701 may then drive, cause, or initiate the relevant actions, e.g., send the information/command "open window" to the window ECU, etc.

FIG. 7 also illustrates example positions at which the sensors (e.g., mmWave sensors, temperature sensor, light sensor, WiFi, camera, proximity sensor, etc.) may be located for monitoring the interior of the vehicle 720. As shown in FIG. 7, the TCU 701 may also include one or more other components X, Y, Z in addition to the sensors, sensor data fusion 740, Network Access Device 744. The three dots after "Sensor . . . " indicate that the sensor array may include any number of additional sensors that can be integrated or combined with the TCU 701. The electronic control unit (ECU) 748 may comprise any ECU that can receive information from the TCU (e.g., Brake, Window, Flash lights, etc.) through a gateway 752 or directly. Electrical connections (broadly, connections) are indicated by arrows between the sensors and sensor data fusion 740, the arrow between the TCU module 700 and ECU 748, and the arrow between the gateway 752 and ECU 748.

Figure 8:
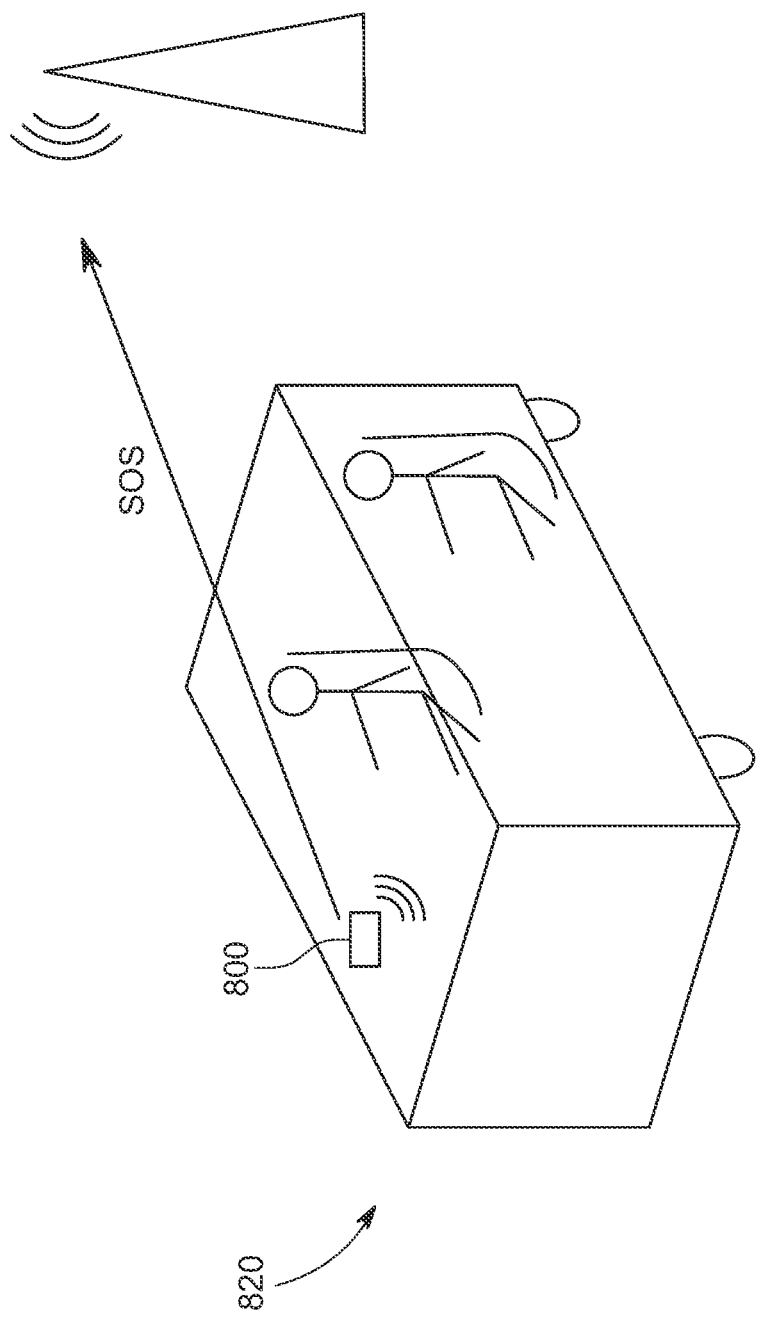
FIG. 8 illustrates a schematic view of a vehicle including a telematics control unit (TCU) having one or more sensors according to an exemplary embodiment, and illustrating that an eCall or SOS has been triggered by the TCU.

FIG. 8 illustrates a vehicle 820 including a TCU module 800 including one or more sensors according to an exemplary embodiment. By way of example, sensors may be integrated into or embedded within a TCU, e.g., placed along the TCU PCB, etc. Or, for example, sensors may be mounted along the bottom and/or one or more side(s) of the TCU module 800. As yet another example, sensors may be electrically connected directly to the TCU, e.g., via wires, cables, board-to-board connectors, etc.

The sensors and the TCU may be configured such that the TCU module 800 is within the gap or spaced defined between the vehicle roof and the roof liner. The sensors are configured for monitoring the vehicle's passenger interior. The TCU module 800 may comprise a variety of sensor types, such as mmWave sensors, temperature sensors, ambient light sensors, biometric sensors, cameras, proximity sensors, WiFi, touch sensors, microphones, etc. For example, the TCU module 800 may include one or more mmWave sensors configured for monitoring health conditions (e.g., heart rate, breathing rate, etc.) of occupants within a vehicle passenger interior. The TCU module 800 may also include one or more temperature sensors configured for monitoring the temperature within the vehicle passenger interior.

FIG. 8 also illustrates an SOS or eCall that has been triggered by the TCU module 800. In this example, the TCU module 800 may be configured to automatically trigger the SOS or eCall when a mmWave sensor has failed to detect a vehicle occupant's heart rate after a predetermined amount of time. The TCU module 800 may also or alternatively be configured to automatically trigger the SOS or eCall when a mmWave sensor has failed to detect a vehicle occupant's respiration rate or breathing rate after a predetermined amount of time, see, for example, FIG. 9 discussed below.

The TCU module 800 may be configured to automatically trigger an eCall if the mmWave sensor cannot detect a heart rate or breathing rate for a vehicle occupant over a certain time period and that occupant is the driver and driving alone. Additionally, or alternatively, if the mmWave sensor cannot detect a heart rate or breathing rate for a vehicle occupant over a certain time period and that occupant is a passenger or the driver but not driving alone, then the TCU may be configured to automatically issue an alert to inform other vehicle occupants. For example, an audible alert or announcement may be broadcast over one or more speakers of the vehicle's sound system. Or, for example, a visual alert or warning may be displayed on one or more displays (e.g., dashboard display, display of an in-vehicle entertainment system, etc.) of the vehicle.

Conventionally, eCalls may be triggered by relying upon accelerometers, airbag deployment in the case of an impact, and/or manual press of eCall button. In the latter case, no eCall will be started without the manual press of the eCall button, such as when the driver is experiencing a heart attack or other health condition rendering the driver unable to manually press the eCall button.

In exemplary embodiments disclosed herein, the TCU module and its sensors may be configured to monitor the health of the vehicle occupant(s) and to automatically trigger an eCall if necessary based on a vehicle occupant's health condition (e.g., failure to detect to heart rate and/or breathing rate over a period of time, other deteriorating health condition, etc.). Additionally, or alternatively, the TCU module and its sensors may be configured to monitor the condition of the driver and to automatically apply the brakes of the vehicle, take over driving of the vehicle by teleoperated driving, or otherwise avoid a crash should the driver's monitored condition indicate an inability of the driver to safely operate the vehicle. Accordingly, exemplary embodiments may be configured to enable various functions, such as automatic triggering of an eCall, automatic crash avoidance by braking and/or steering, etc. In exemplary embodiments, the TCU module may be configured to communicate with one or more or all of the electronic control units (ECUs) of the vehicle to enable various functionality. The TCU module and its sensors may be configured for other possible uses in other exemplary embodiments as a wide variety of sensors may be combined or integrated with (e.g., embedded within, electrically connected directly to, mounted along a bottom/side of, etc.) the TCU.

Figure 9:
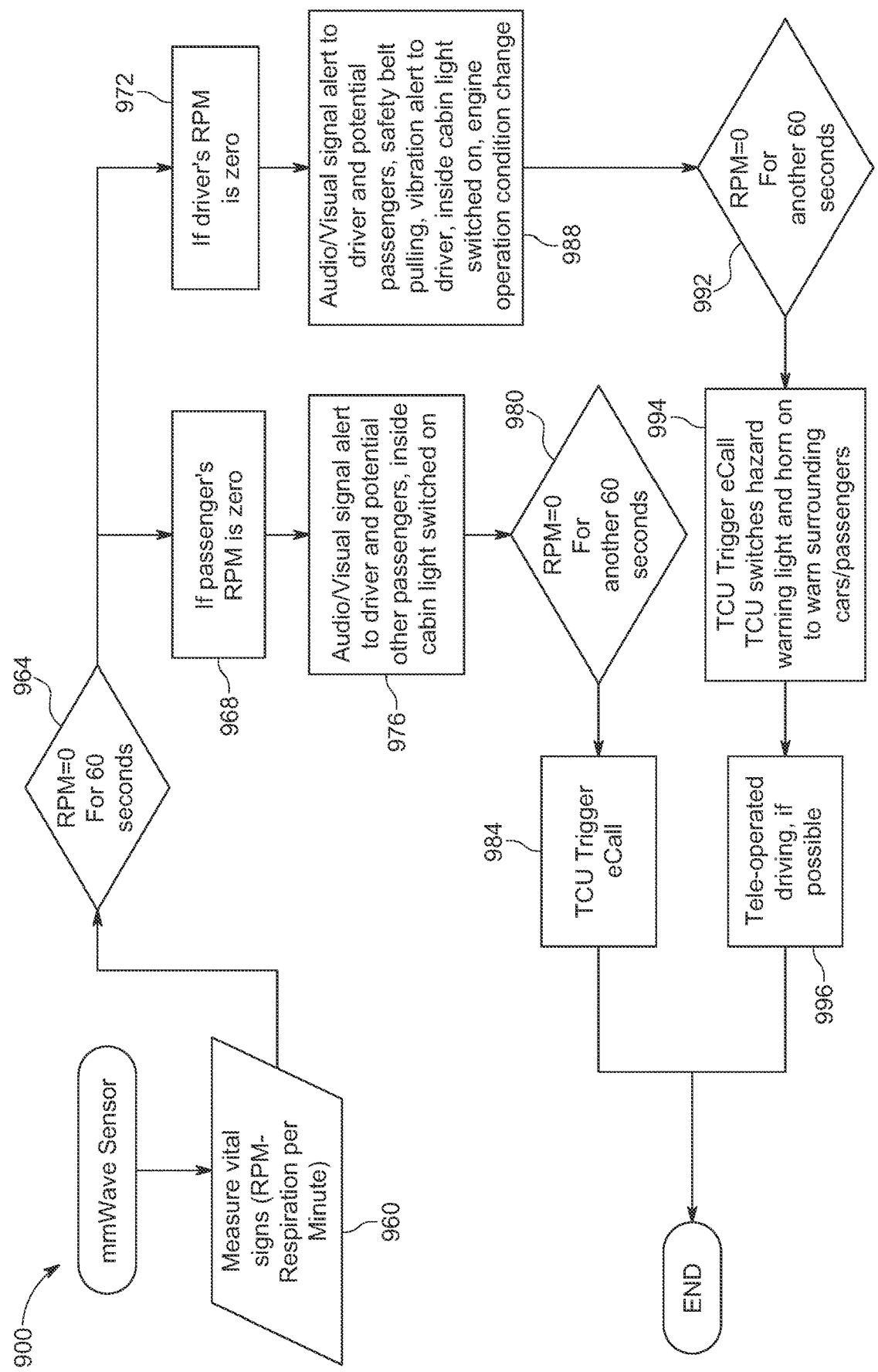
FIG. 9 is a process flow diagram showing various steps that may be taken before a TCU triggers an eCall when a mmWave sensor has measured zero respirations per minute (RPM) for a driver or passenger of a vehicle.

FIG. 9 is a process flow diagram showing various steps of an exemplary method 900 that may be taken before a TCU triggers an eCall when a mmWave sensor has measured zero respirations per minute (RPM) for the driver or a passenger of a vehicle. At 960, a mmWave sensor measures vital signs of the vehicle's occupant(s) including respirations per minute (RPM) for sixty seconds. If the RPM of a vehicle occupant is zero for sixty seconds as determined at 964, then a determination is made whether the occupant is the passenger at 968 or the driver at 972.

If it is determined that the passenger's RPM is zero at 968, then an audio/visual signal alert is generated to alert the driver and potentially other vehicle passengers at 976. The audio/visual signal alert may include switching on the inside cabin light, etc. If the RPM of the passenger is zero for another sixty seconds as determined at 980, then the TCU triggers an eCall at 984.

If it is determined that the driver's RPM is zero at 972, then an audio/visual signal alert is generated to alert the driver and potentially other vehicle passengers at 988. The audio/visual signal alert may include safety belt pulling, a vibration alert to the driver, switching on the inside cabin light, an engine operation condition change, etc. If the RPM of the driver is zero for another sixty seconds as determined at 992, then the TCU module triggers an eCall at 994. Also at 994, the TCU module may switch the vehicle's hazard lights on and sound the vehicle's horn to warn surrounding cars and passengers therein. Step 996 includes tele-operated driving of the vehicle, if possible.

In exemplary embodiments, the TCU module and its sensors may be adjacent or underneath (e.g., directly underneath, etc.) a vehicular antenna assembly (e.g., V2X smart antenna assembly, a multiband multiple input multiple output (MIMO) vehicular antenna assembly, etc.). The antenna assembly and its mounting mechanism may be configured to allow the antenna assembly to be installed and fixedly mounted to a body wall of a vehicle after being inserted into a mounting hole in the body wall from an external side of the vehicle and nipped from an interior compartment side of the vehicle. Also from inside the vehicle, the TCU may be coupled to the vehicular antenna assembly, e.g., via a mounting bracket, etc. Electrical connectors (e.g., board-to-board (B2B) connectors, etc.) may be used to provide an electrical connection between the TCU and the antenna assembly.

By way of example, the TCU module and its sensors may be used with a vehicular antenna assembly that includes a plurality of antenna elements operable with different frequencies and/or bandwidths. The plurality of antenna elements may include one or more of a first or primary cellular antenna (e.g., stamped primary cellular antenna element, etc.), a second or secondary cellular antenna (e.g., stamped secondary cellular antenna element, etc.), a remote keyless entry (RKE) antenna (e.g., coil radiator, PCB antenna, etc.), a Bluetooth Low Energy (BLE) antenna, a Global Navigation Satellite System (GNSS) antenna (e.g., patch antenna, etc.), a Dedicated Short Range Communication (DSRC) antenna, a V2X antenna, a Satellite Digital Audio Radio Service (SDARS) antenna (e.g., patch antenna, etc.), etc.

Continuing with this example, the primary cellular antenna may be monopole antenna (e.g., stamped metal wide band monopole antenna mast, etc.) configured to be operable for both receiving and transmitting communication signals within one or more cellular frequency bands (e.g., Long Term Evolution (LTE), etc.). The secondary cellular antenna may be configured to be operable for receiving (but not transmitting) communication signals within one or more cellular frequency bands (e.g., LTE, etc.).

The GNSS antenna may comprise a patch antenna configured to be operable for receiving Global Navigation Satellite System (GNSS) signals or frequencies (e.g., Global Positioning System (GPS), BeiDou Navigation Satellite System (BDS), the Russian Global Navigation Satellite System (GLONASS), Doppler Orbitography and Radiopositioning Integrated by Satellite (DORIS), other satellite navigation system frequencies, etc.). The SDARS antenna may comprise a patch antenna configured to be operable for receiving SiriusXM satellite radio signals or frequencies. The GNSS and SDARS patch antennas may be horizontally spaced apart from each other, or the GNSS and SDARS patch antennas may be in a vertically stacked arrangement with the GNSS patch antenna stacked on top of the SDARS patch antenna.

In this example, the services for DSRC, AM/FM, DAB, LTE, GNSS, satellite radio, and V2X may be located within a single roof-mount antenna system. The antenna system may be configured to enable communication between the vehicle and environment (Vehicle-to-Infrastructure (V2I) and/or between the vehicle and another vehicle (Vehicle-to-Vehicle (V2V)). The TCU module may be configured to be in communication with and be connected with the antenna assembly over an Ethernet interface. The TCU module may be configured to provide internet access service (e.g., wireless connectivity, internet browsing capability, etc.) to passengers in the vehicle. Components of the TCU module may generally include a microprocessor or microcontroller, a modem (e.g., LTE 4G modem, etc.), a Wi-Fi module, a Bluetooth/Bluetooth low energy (BT/BLE) module, and Ethernet interface(s). The microprocessor or microcontroller may be generally configured to process data received from the antenna assembly. The TCU module may be configured to relay DSRC related digital information from the antenna assembly to the vehicle's HMI (human machine interface) system via Wi-Fi and/or Ethernet. The Ethernet interface may be configured to communicate data between the antenna assembly and the TCU. By way of example, the HMI system may use a visible warning on a display and/or an audible warning (e.g., a chime, buzzer, etc.) depending on the digital information it received.

The various antenna elements disclosed above are examples only as the TCU module and its sensors may be used with other antenna assemblies including more or less antenna and/or antennas operable with different frequencies and/or bandwidths, etc. Accordingly, the TCU module and its sensors should not be limited to use with only one particular type of vehicular antenna assembly or any one particular type of vehicle.

In exemplary embodiments, a telematics control unit comprises a sensor array including one or more sensors and configured to be operable for monitoring a passenger interior of a vehicle. The sensor array including the one or more sensors are combined and/or integrated with the telematics control unit, whereby the telematics control unit including the sensor array are operable and/or positionable within the vehicle collectively as a single combined and/or integrated unit.

In an exemplary embodiment, the one or more sensors of the sensor array comprise a plurality of different types of separate sensors. The telematics control unit includes one or more processors configured to be operable for processing sensor data from the plurality of different types of separate sensors. The telematics control unit is configured to communicate with one or more electronic control units of the vehicle to automatically initiate one or more actions in response to the processing of the sensor data.

In an exemplary embodiment, at least one of the one or more sensors of the sensor array is: embedded within the telematics control unit; along a printed circuit board of the telematics control unit, directly connected with the telematics control unit by one or more of a wire, cable, and/or a board-to-board connector; mounted along a bottom or a side of the telematics control unit; and/or disposed within an interior space defined by a housing of the telematics control unit.

In an exemplary embodiment, the one or more sensors of the sensor array comprise a plurality of different types of separate sensors including one or more of a mmWave sensor, a temperature sensor, an ambient light sensor to detect visibility, a glass breaking sensor to detect breaking of a vehicle window, an airbag sensor to detect excitation of an airbag, a biometric sensor, a camera, a proximity sensor, WiFi, a touch sensor, and a microphone.

In an exemplary embodiment, the telematics control unit including the sensor array are configured to be operable for monitoring one or more vital signs of one or more occupants within the passenger interior of the vehicle.

In an exemplary embodiment, the one or more sensors comprise one or more mmWave sensors. The telematics control unit including the one or more mmWave sensors are configured to be operable for monitoring heart rate and/or respiration rate of one or more occupants within the passenger interior of the vehicle.

In an exemplary embodiment, the telematics control unit including the sensor array are configured to be operable for: monitoring heart rate and/or respiration rate of one or more occupants within the passenger interior of the vehicle; and automatically triggering one or more actions in response to a failure to detect the heart rate and/or respiration rate of at least one occupant within the passenger interior after a predetermined amount of time. In this exemplary embodiment, the telematics control unit may be configured to automatically trigger an eCall in response to the failure to detect the heart rate and/or respiration rate of the at least one occupant within the passenger interior after the predetermined amount of time. The telematics control unit may be configured to: automatically trigger one or more alerts to alert the driver and/or one or more other occupants within the passenger interior in response to a first failure to detect the heart rate and/or respiration rate of the at least one occupant after a first predetermined amount of time; and automatically trigger an eCall in response to a second failure to detect the heart rate and/or respiration rate of the at least one occupant within the passenger interior after a second predetermined amount of time. The one or more alerts may include one or more of a safety belt pulling, a vibration alert to the driver, switching on an inside cabin light, an engine operation condition change, an audible alert broadcast over one or more speakers of a sound system of the vehicle, and a visual alert displayed on a dashboard display or display of an in-vehicle entertainment system. When the at least one occupant is the driver, the telematics control unit may be configured to automatically trigger the eCall and one or more additional actions in response to the second failure to detect the heart rate and/or respiration rate of the driver of the vehicle after the second predetermined amount of time. The one or more additional actions may include one or more of: automatically switching on hazard lights of the vehicle and/or automatically sounding a horn of the vehicle to thereby warn nearby vehicles and/or other occupants within the passenger interior of the vehicle; and/or automatic crash avoidance by braking and/or steering of the vehicle.

In an exemplary embodiment, the one or more sensors comprise one or more temperature sensors. The telematics control unit including the one or more temperature sensors are configured to be operable for monitoring temperature within the passenger interior of the vehicle and for automatically triggering one or more actions in response to detection of at least one occupant in the passenger interior and a temperature of the passenger interior above a predetermined maximum temperature. In this exemplary embodiment, the telematics control unit may be configured to initiate automatic opening of a window and/or generation of an alert when at least one occupant is detected in the passenger interior and the temperature of the passenger interior is above the predetermined maximum temperature.

In an exemplary embodiment, the telematics control unit module including the sensor array are configured to be positioned collectively as the single combined and/or integrated unit along or in a ceiling of the vehicle so as to provide a line of sight between the one or more sensors and occupants within the passenger interior of the vehicle.

In exemplary embodiments, a method comprises providing a telematics control unit module including a sensor array configured to be operable for monitoring a passenger interior of a vehicle. The sensor array includes one or more sensors combined and/or integrated with the telematics control unit, whereby the telematics control unit including the sensor array are operable and/or positionable within the vehicle collectively as a single combined and/or integrated unit.

In an exemplary embodiment, the one or more sensors of the sensor array comprise a plurality of different types of separate sensors. The method further includes: processing, via one or more processors of the telematics control unit module, sensor data from the plurality of different types of separate sensors; and automatically initiating, via the telematics control unit module, one or more actions in response to the processing of the sensor data.

In an exemplary embodiment, providing the telematics control unit module including the sensor array comprises one or more of: embedding at least one of the one or more sensors of the sensor array within the telematics control unit; positioning at least one of the one or more sensors of the sensor array along a printed circuit board of the telematics control unit; directly connecting at least one of the one or more sensors of the sensor array with the telematics control unit by one or more a wire, cable, and/or a board-to-board connector; mounting at least one of the one or more sensors of the sensor array along a bottom or a side of the telematics control unit; and/or disposing at least one of the one or more sensors of the sensor array within an interior space defined by a housing of the telematics control unit.

In an exemplary embodiment, the method includes monitoring, via the telematics control unit module including the sensor array, one or more vital signs of one or more occupants within the passenger interior of the vehicle.

In an exemplary embodiment, the method includes monitoring, via the telematics control unit module including the sensor array, heart rate and/or respiration rate of one or more occupants within the passenger interior of the vehicle; and automatically triggering, via the telematics control unit module, one or more actions in response to a failure to detect the heart rate and/or respiration rate of at least one occupant within the passenger interior after a predetermined amount of time. In this exemplary embodiment, the method may include automatically triggering an eCall, via the telematics control unit module, in response to the failure to detect the heart rate and/or respiration rate of the at least one occupant within the passenger interior after the predetermined amount of time. The method may include: automatically triggering, via the telematics control unit module, one or more alerts to alert the driver and/or one or more other occupants within the passenger interior in response to a first failure to detect the heart rate and/or respiration rate of the at least one occupant after a first predetermined amount of time; and automatically triggering, via the telematics control unit, an eCall in response to a second failure to detect the heart rate and/or respiration rate of the at least one occupant within the passenger interior after a second predetermined amount of time. When the at least one occupant is the driver, the method may include automatically triggering, via the telematics control unit module, the eCall and one or more additional actions in response to the second failure to detect the heart rate and/or respiration rate of the driver of the vehicle after the second predetermined amount of time. The one or more additional actions may include one or more of: automatically switching on hazard lights of the vehicle and/or automatically sounding a horn of the vehicle to thereby warn nearby vehicles and/or other occupants within the passenger interior of the vehicle; and/or automatic crash avoidance by braking and/or steering of the vehicle.

In an exemplary embodiment, the method includes: monitoring, via the telematics control unit module including the sensor array, temperature within the passenger interior of the vehicle; and automatically triggering, via the telematics control unit module, one or more actions in response to detection of at least one occupant in the passenger interior and a temperature of the passenger interior above a predetermined maximum temperature.

In an exemplary embodiment, providing the telematics control unit module including the sensor array comprises positioning the telematics control unit module and the sensor array collectively as the single integrated combined unit along or in a ceiling of the vehicle so as to provide a line of sight between the one or more sensors and occupants within the passenger interior of the vehicle.

The foregoing description of the embodiments has been provided for purposes of illustration and description. It is not intended to be exhaustive or to limit the disclosure. Individual elements, intended or stated uses, or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

We claim:

1. A telematics control unit (TCU) module comprising:
a TCU; and
a sensor array configured to be operable for monitoring a passenger interior of a vehicle, the sensor array integrated with the telematics control unit, whereby the telematics control unit module, including the sensor array, is positionable within the vehicle as a single integrated unit; wherein the TCU module is configured, in operation, to:
monitor heart rate and/or respiration rate of one or more occupants within the passenger interior of the vehicle;
automatically trigger one or more alerts to alert a driver and/or one or more other occupants within the passenger interior in response to a first failure to detect the heart rate and/or respiration rate of at least one occupant after a first predetermined amount of time; and
automatically trigger an eCall in response to a second failure to detect the heart rate and/or respiration rate of the at least one occupant within the passenger interior after a second predetermined amount of time.

2. The TCU module of claim 1, wherein the sensor array comprise a plurality of different types of separate sensors; and
the telematics control unit includes one or more processors configured to be operable for processing sensor data from the plurality of different types of separate sensors.

3. The TCU module of claim 2, wherein the telematics control unit is configured to communicate with one or more electronic control units of the vehicle to automatically initiate one or more actions in response to the processing of the sensor data.

4. The TCU module of claim 1, wherein a sensor of the sensor array is:
embedded within the telematics control unit;
along a printed circuit board of the telematics control unit, directly connected with the telematics control unit by one or more a wire, cable, and/or a board-to-board connector;
mounted along a bottom or a side of the telematics control unit; and/or
disposed within an interior space defined by a housing of the telematics control unit.

5. The TCU module of claim 1, wherein the sensor array comprises a plurality of different types of separate sensors including one or more of a mmWave sensor, a temperature sensor, an ambient light sensor to detect visibility, a glass breaking sensor to detect breaking of a vehicle window, an airbag sensor to detect excitation of an airbag, a biometric sensor, a camera, a proximity sensor, WiFi, a touch sensor, and a microphone.

6. The TCU module of claim 1, wherein the TCU module is configured, in operation, to monitor one or more vital signs of one or more occupants within the passenger interior of the vehicle.

7. The TCU module of claim 1, wherein when the at least one occupant is the driver of the vehicle, the TCU module is configured, in operation, to automatically trigger the eCall and one or more additional actions in response to the second failure to detect the heart rate and/or respiration rate of the driver of the vehicle after the second predetermined amount of time, and wherein the one or more additional actions include one or more of automatically switching on hazard lights of the vehicle and/or automatically sounding a horn of the vehicle to thereby warn nearby vehicles and/or other occupants within the passenger interior of the vehicle.

8. The TCU module of claim 1, wherein when the at least one occupant is the driver of the vehicle, the TCU module is configured, in operation, to automatically trigger the eCall and one or more additional actions in response to the second failure to detect the heart rate and/or respiration rate of the driver of the vehicle after the second predetermined amount of time, and wherein the one or more additional actions include automatic crash avoidance by braking and/or steering of the vehicle.

9. The TCU module of claim 1, wherein the one or more alerts include one or more of a safety belt pulling, a vibration alert to the driver, switching on an inside cabin light, an engine operation condition change, an audible alert broadcast over one or more speakers of a sound system of the vehicle, and a visual alert displayed on a dashboard display or display of an in-vehicle entertainment system.

10. The TCU module of claim 1, wherein when the at least one occupant is the driver of the vehicle, the TCU module is configured to automatically trigger the eCall and one or more additional actions in response to the second failure to detect the heart rate and/or respiration rate of the driver of the vehicle after the second predetermined amount of time, and wherein the one or more additional actions include one or more of:
automatically switching on hazard lights of the vehicle and/or automatically sounding a horn of the vehicle to thereby warn nearby vehicles and/or other occupants within the passenger interior of the vehicle; and/or
automatic crash avoidance by braking and/or steering of the vehicle.

11. The TCU module of claim 1, wherein:
the sensor array comprise one or more temperature sensors; and
the TCU module including the one or more temperature sensors are configured to be operable for monitoring temperature within the passenger interior of the vehicle and for automatically triggering one or more actions in response to detection of at least one occupant in the passenger interior and a temperature of the passenger interior above a predetermined maximum temperature.

12. The TCU module of claim 11, wherein the TCU module is configured to initiate automatic opening of a window and/or generation of an alert when at least one occupant is detected in the passenger interior and the temperature of the passenger interior is above the predetermined maximum temperature.

13. The TCU module of claim 1, wherein the TCU module is positioned in a ceiling of the vehicle so as to provide a line of sight between at least one sensor of the sensor array and occupants within the passenger interior of the vehicle.

14. A method comprising:
providing a telematics control unit (TCU) module including a TCU and a sensor array configured to monitor a passenger interior of a vehicle, the sensor array integrated with the TCU; and
positioning the TCU module within the vehicle as a single unit;
wherein the method includes:
monitoring, via the TCU module, heart rate and/or respiration rate of one or more occupants within the passenger interior of the vehicle;
automatically triggering, via the TCU module, one or more alerts to alert a driver and/or one or more other occupants within the passenger interior in response to a first failure to detect the heart rate and/or respiration rate of at least one occupant after a first predetermined amount of time; and
automatically triggering, via the TCU module, an eCall in response to a second failure to detect the heart rate and/or respiration rate of the at least one occupant within the passenger interior after a second predetermined amount of time.

15. The method of claim 14, wherein the sensor array comprise a plurality of different types of separate sensors and the method further includes:
processing, via one or more processors of the TCU module, sensor data from the plurality of different types of separate sensors; and
automatically initiating, via the TCU module, one or more actions in response to the processing of the sensor data.

16. The method of claim 14, wherein providing the TCU module comprises mounting a sensor of the sensor array along a bottom or a side of the TCU.

17. The method of claim 14, wherein the method includes monitoring, via the TCU module, one or more vital signs of one or more occupants within the passenger interior of the vehicle.

18. The method of claim 14, wherein the method includes initiating, via the TCU module, automatic opening of a window and/or generation of an alert when at least one occupant is detected in the passenger interior and a temperature of the passenger interior is above a predetermined maximum temperature.

19. The method of claim 14, wherein the one or more alerts include one or more of a safety belt pulling, a vibration alert to the driver, switching on an inside cabin light, an engine operation condition change, an audible alert broadcast over one or more speakers of a sound system of the vehicle, and a visual alert displayed on a dashboard display or display of an in-vehicle entertainment system.

20. The method of claim 14, wherein when the at least one occupant is the driver of the vehicle, the method includes:
automatically switching on hazard lights of the vehicle and/or automatically sounding a horn of the vehicle to thereby warn nearby vehicles and/or other occupants within the passenger interior of the vehicle; and/or
automatically initiating crash avoidance by braking and steering the vehicle to a side of a road.

* * * * *